United States Patent
Rahn et al.

(10) Patent No.: US 7,792,593 B2
(45) Date of Patent: Sep. 7, 2010

(54) METHOD AND SYSTEM FOR PATIENT-SPECIFIC PRODUCTION OF A CARDIAC ELECTRODE

(75) Inventors: Norbert Rahn, Forchheim (DE); Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 440 days.

(21) Appl. No.: 11/600,976

(22) Filed: Nov. 17, 2006

(65) Prior Publication Data

US 2008/0119901 A1    May 22, 2008

(51) Int. Cl.
*A61N 1/05* (2006.01)
(52) U.S. Cl. .................... 607/122; 600/427; 700/118
(58) Field of Classification Search ............ 600/410, 600/411, 427, 429, 439; 607/119, 120, 129, 607/122; 700/118
See application file for complete search history.

(56) References Cited

U.S. PATENT DOCUMENTS

| | | | |
|---|---|---|---|
| 2004/0026808 A1* | 2/2004 | Litschko et al. | 264/40.1 |
| 2004/0087850 A1* | 5/2004 | Okerlund et al. | 600/407 |
| 2005/0197731 A1* | 9/2005 | Ahn et al. | 700/130 |
| 2006/0017749 A1* | 1/2006 | McIntyre et al. | 345/664 |
| 2007/0118243 A1* | 5/2007 | Schroeder et al. | 700/118 |

* cited by examiner

*Primary Examiner*—Carl H Layno
*Assistant Examiner*—Pamela M Bays
(74) *Attorney, Agent, or Firm*—Schiff Hardin LLP

(57) ABSTRACT

In a method and system for patient-specific production of a cardiac electrode lead, a 3D representation of the coronary sinus vessel tree is segmented to indicate the interior surface thereof and a representative line from an opening of the coronary sinus vessel tree to an implantation site for the electrode lead, and a computerized model of the electrode is generated that includes deformation properties of the mechanical structure of the electrode lead. A computerized virtual implantation of the electrode through the 3D representation of the coronary sinus vessel tree is implemented using the model and the internal surface and the representative line from which determination is made as to whether an electrode conforming to the model can be guided to and implanted at the implantation site in a medically acceptable manner, or whether modification of the electrode lead is necessary.

24 Claims, 4 Drawing Sheets

METHOD AND SYSTEM FOR PATIENT-SPECIFIC PRODUCTION OF A CARDIAC ELECTRODE

BACKGROUND OF THE INVENTION

1. Field of the Invention

The present invention concerns a system and a method for producing a patient-specific cardiac electrode, and in particular for production of a cardiac electrode in a biventricular pacing system.

2. Description of the Prior Art

Tachycardia and bradycardia can be treated therapeutically with conventional pacing. Biventricular pacing therapy, also called cardiac resynchronization therapy (CRT) is used to artificially produce a synchronization between the right ventricle and the left ventricle in patients in whom such synchronization is not present, due to a cardiac pathology or insufficiency.

A biventricular pacing system requires three electrodes, two of which are typically implanted in the right atrium and in the right ventricle, respectively, at locations at which conventional cardiac pacemaker electrodes are normally implanted. The third electrode is positioned in a side branch of the coronary venous tree. For this purpose, an implantation tool such as a catheter, carrying the electrode, is navigated (guided) through the coronary sinus into a communicating side branch, and the electrode is anchored into place at an appropriate location.

For optimal stimulation of the left ventricle (LV) it is important that the anchoring (implantation) site of the aforementioned third electrode be optimally selected, and it is also important that the third electrode be optimally adapted, with regard to its length and curvature, to the individual anatomy of the patient.

There are various conventional techniques that are known for supporting implantation of the CRT electrodes. A commercially available guide wire from Stereotaxix, is magnetically controllable for facilitating navigation in the coronary venous tree. The possibilities for imaging for identification of a suitable implantation site, and guidance to that site, are limited with such known methods.

SUMMARY OF THE INVENTION

An object of the present invention is to provide a method and system that allow a cardiac electrode, in particular a cardiac electrode in a biventricular pacing system, to be produced in a patient-specific manner, so that the electrode is adapted to the individual patient anatomy and morphology.

In accordance with the present invention, a procedure is implemented, supported by 3D imaging of the left ventricle and the coronary sinus vessel tree, to identify an optimal anchoring site. A suitable method and system for this purpose are disclosed in U.S. application Ser. No. 11/671,549 filed Feb. 6, 2007 and assigned to the same assignee, Siemens Aktiengesellschaft, as the present application.

In accordance with the present invention, after the target implantation site has been identified or selected, a computer model of the coronary venous tree, or at least the branch thereof containing the implantation site, is generated, and the coronary venous branch in the image in which the electrode is to be implanted is segmented. After the segmentation, a representative line, such as a center line, of the course or path of this vessel branch is determined from the mouth or opening of the coronary sinus vein up to the implantation site in that branch.

A 3D model of the electrode is then generated based on this representative line. The model is adapted to the representative line with regard to the curvature and length of the electrode and the segmentation of the, vessel surface with regard to thickness. This model of the electrode is used as a planning tool for guidance and placement of the pacemaker electrode at the implantation site in a virtual implantation procedure. Via an interactive interface, preferably a tactile interface, feedback is generated to a physician during the virtual implantation procedure dependent on the intensity of contact with the interior vessel wall, the curvature of the vessel, the torsion and the friction encountered with respect to the vessel wall by the electrode model.

If the virtual implantation procedure is able to be conducted in a medically acceptable manner to the implantation site, the model of the pacemaker electrode is considered to be optimal. If not, modifications to the model can be made and the virtual implantation procedure can be repeated with the modified model. This can be iteratively repeated until a satisfactory electrode configuration is achieved.

"Medically acceptable" means that risks to the patient are minimized or reduced to an inconsequential level and that no extraordinary difficulties are encountered in the implantation.

Once the satisfactory electrode configuration is achieved, the final model corresponding to the satisfactory configuration is used to produce an actual electrode, that is then used in the actual implantation procedure.

DESCRIPTION OF THE PREFERRED EMBODIMENTS

Figure 1:
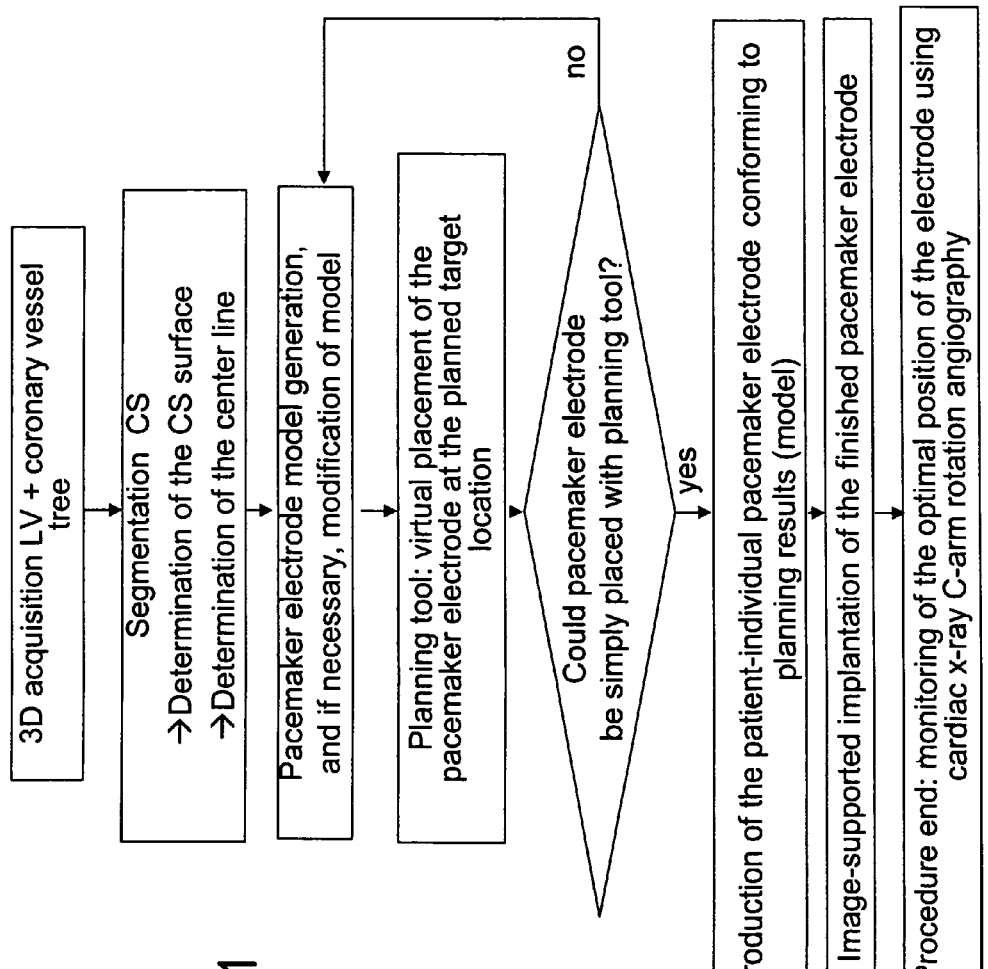
FIG. 1 is a flowchart showing the basic steps in accordance with the inventive method, that are implemented by a system in accordance with the present invention.
Figure 2:
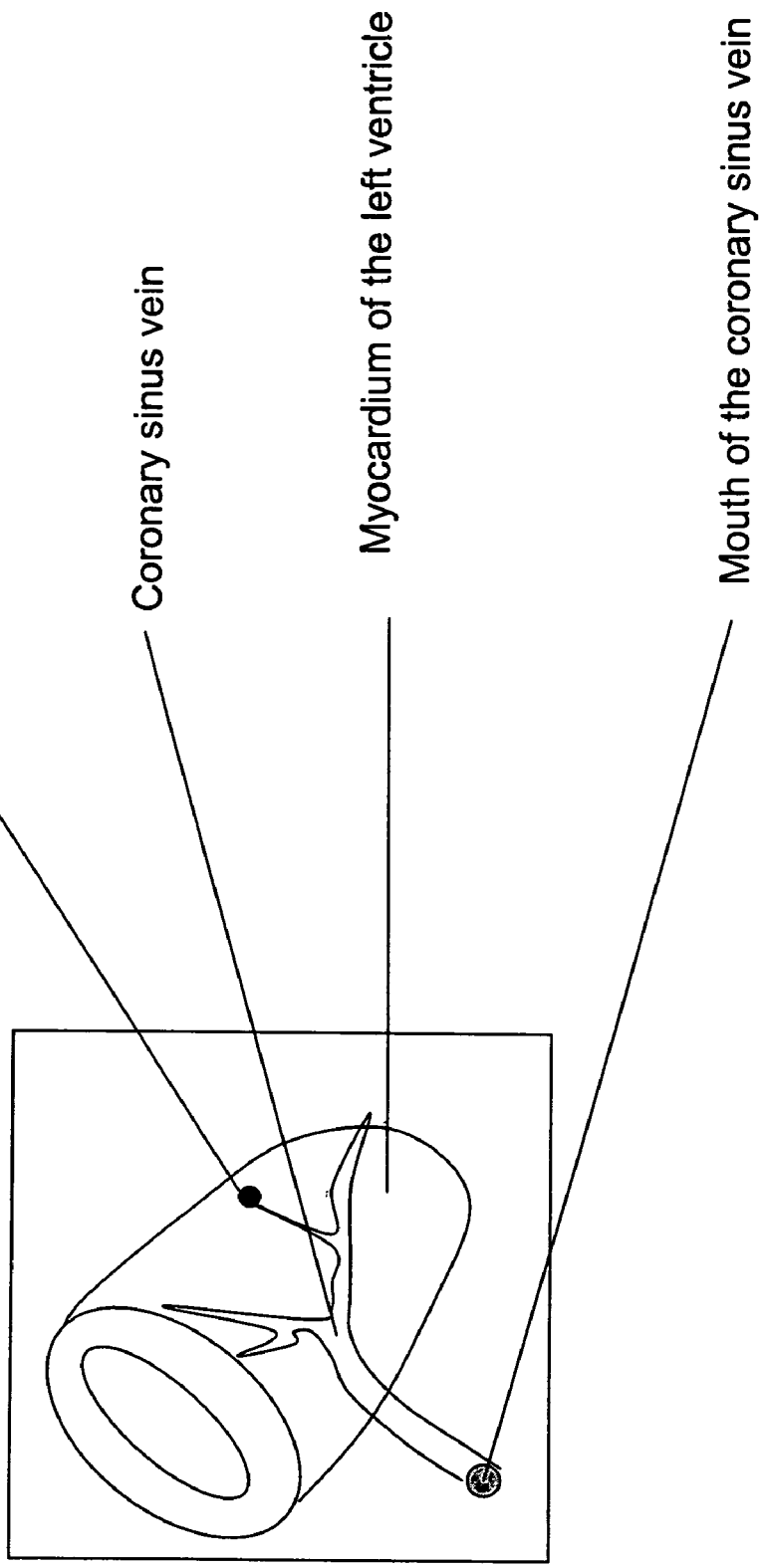
FIG. 2 schematically illustrates an image of the left ventricle and the coronary sinus vessel system used to identify a target implantation site in accordance with the present invention.
Figure 3:
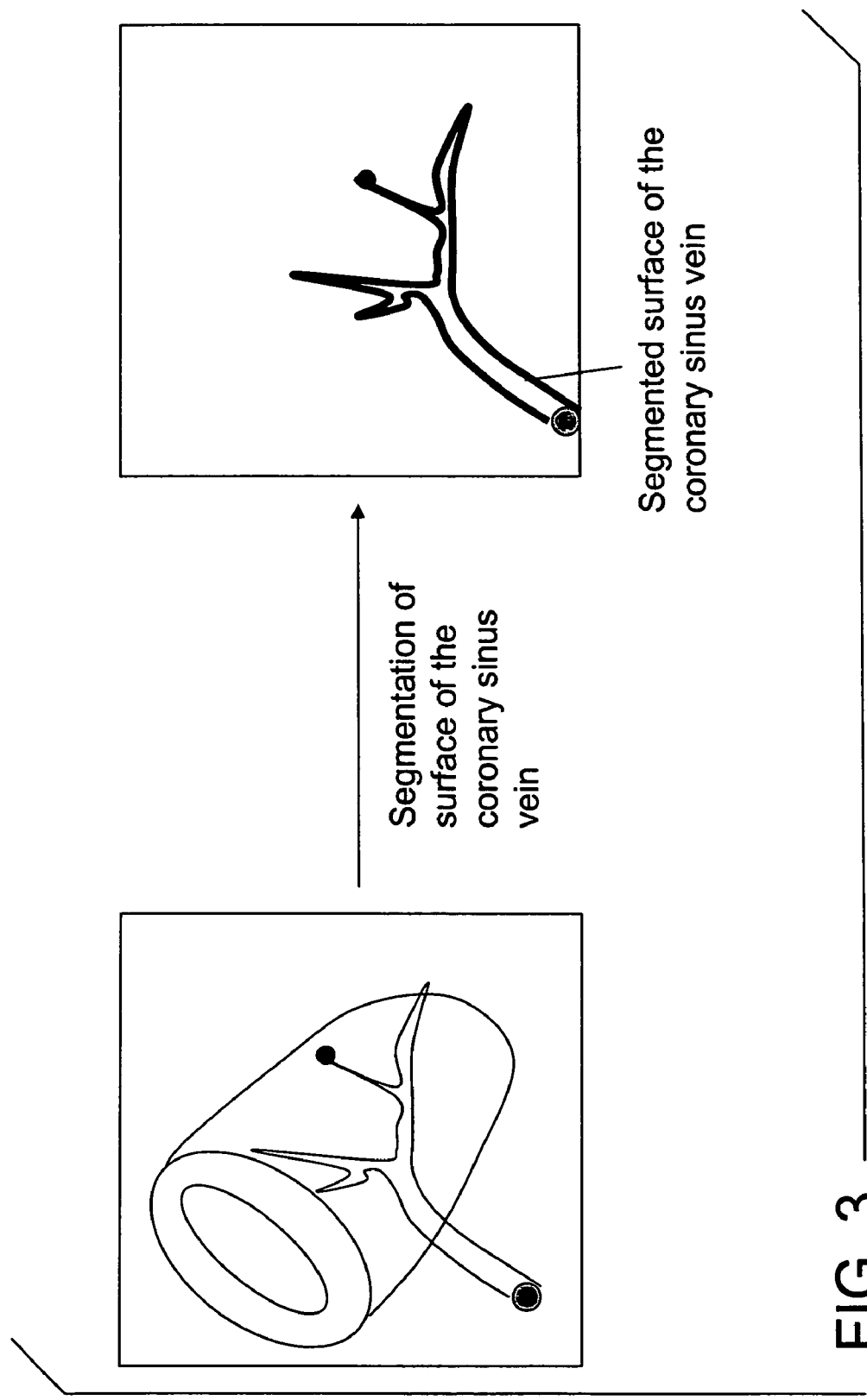
FIG. 3 illustrates the segmentation of the surface of the coronary sinus vein from the image of FIG. 2.
Figure 4:
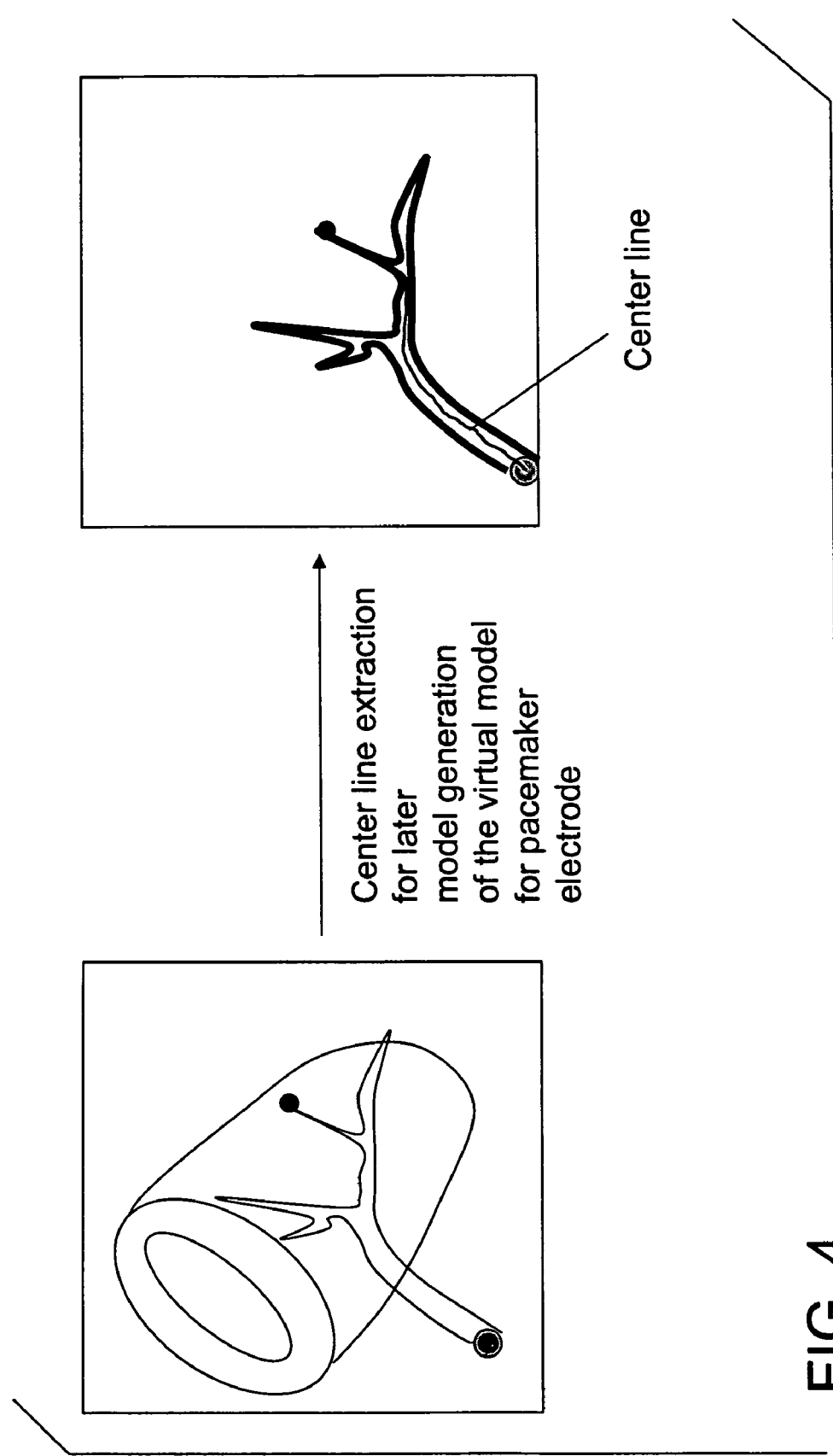
FIG. 4 schematically illustrates an embodiment of the invention making use of center line extraction of the coronary sinus vein and a branch thereof for generating a virtual model of an electrode.

Using a suitable technique and system, such as those disclosed in the aforementioned simultaneously filed application, an optimal anchoring site for the third electrode of a biventricular pacing system is identified in a branch of the coronary sinus vessel system of a patient. This is achieved using 3D image data, or optionally 4D data, representing a time-resolved dynamic image of the region of interest, thereby allowing heart movement to be taken into account in the planning of the implantation of the electrode. Alternatively, two 3D data sets can be obtained, one of which being acquired and reconstructed in the systolic phase of the heart movement and the other being acquired and reconstructed in the diastolic phase of the heart movement.

From the aforementioned 3D data, a computerized model of the coronary venous tree, or a branch thereof is generated. The coronary venous branch in which the electrode is to be implanted is segmented. After the segmentation a representative line, such as a center line, of the vessel course is determined, from the mouth or opening of the coronary sinus vein up to the implantation site in the coronary venous branch that communicates with the coronary sinus vein.

Alternatively, instead of a center line other more complex models for describing the path of the coronary branch can be used.

If time-resolved (4D) data were used to identify the implantation site, the segmentation and center line extraction can ensue for each individual heart phase and the center line can be considered as an average value. Alternatively, a maximum of the center line in the systolic phase can be identified, and a maximum of the center line in the diastolic phase can be determined, and these maxima can be averaged.

A 3D computerized model of the electrode is generated based on the aforementioned center line of the appropriate coronary venous branch. This model is adapted to the center line with regard to curvature and length of the electrode, and to the segmentation of the vessel surface with regard to thickness, so that the electrode can be optimally guided through the coronary vessel tree to the implantation site. The model can be represented as a network of polygons, for example triangles. Deformation properties such as curvature resistance and torsion resistance can also be incorporated in the model.

The generated model of the electrode is used as a planning tool for guidance and placement of the electrode in the context of a virtual implantation procedure.

Inputs for the virtual implantation procedure in the planning tool are the segmented surface of the coronary sinus vessel tree as well as the aforementioned model of the electrode.

In the virtual implantation procedure, feedback, preferably tactile or haptic feedback, is generated and provided to the user via an interface during the virtual implantation procedure, depending on the intensity of contact of the electrode model with the interior vessel wall, curvature of the electrode, torsion of the electrode with regard to the interior vessel wall, and friction with regard to the interior vessel wall.

If the outcome of the virtual implantation procedure indicates that the model electrode can be simply guided to the intended implantation site and optimally placed at that site, the electrode model is considered to be satisfactory. If the result of the virtual implantation procedure indicates a difficulty in bringing the electrode model to the implantation site and/or anchoring the electrode model at the implantation site, a modified model can be generated and the virtual implantation procedure repeated, until a satisfactory implantation and anchoring are achieved.

After an optimal model of the electrode is achieved, an actual pacemaker electrode is produced according to the model.

For this purpose, it is possible that an apparatus for producing the electrode can be provided at the planning location, so the computerized model can be directly transferred to the production apparatus. If the production apparatus is not located at the planning site, the electronic data representing the electrode model can be transferred to the production apparatus by any suitable data transmission arrangement, such as the Internet.

The actual electrode produced from the model is then implanted in the subject at the aforementioned implantation site.

If an active navigation system or other automatic guidance system is used for directing the electrode in the actual implantation procedure, parameters from the virtual implantation procedure, for example an optimal path ultimately determined with the satisfactory model, can be used to control the implantation or to detect deviation of the current position of the electrode during the implantation procedure from the ideal guidance path. For this purpose, any known technique can be employed for identifying the position of at least a portion, such as the tip, of an implantation tool used to implant the electrode.

After the implantation of the actual electrode is completed, a check by imaging can be made to determine that the placement of the electrode is optimal.

The inventive method and system not only result in an electrode that is specifically adapted to the patient in whom it is to be implanted, but also achieve this result with a reduced procedure time, reduced use of contrast agent, a reduced exposure of the patient to x-rays, and an overall better therapy result is achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing a patient-specific implantable pacemaker electrode, comprising the steps of:

using an electronic 3D representation of the coronary sinus vessel tree of a patient in whom a pacemaker electrode is to be implanted, said 3D representation including an indication of an implantation site in the coronary sinus vessel tree for a pacemaker electrode having a mechanical structure comprising an elongate lead body terminating in an electrode tip segmenting the 3D representation of the coronary sinus vessel tree to visually indicate the interior surface of the coronary sinus vessel tree and a representative line from an opening of the coronary sinus vessel tree to the implantation site;

generating a computerized model of only of said mechanical structure of said electrode, and including computerized deformation properties in said model that model mechanical behavior of said electrode in response to mechanical influences on said mechanical structure;

conducting a computerized virtual implantation of said electrode through said 3D representation of said coronary sinus vessel tree to said implantation site using at least said model and said internal surface and including simulating deformation of said electrode caused by a size and shape of said coronary sinus vessel tree and said deformation information representative line;

from said deformation in said virtual implantation, making an implantation determination as to whether an electrode conforming to said model can be guided to and implanted at said implantation site in a medically acceptable manner;

if said implantation determination is positive, producing an actual electrode conforming to said model; and if said implantation determination is negative, iteratively modifying said model and repeating said virtual implantation until a positive implantation determination is achieved by a last-modified model, and producing an actual electrode conforming to said last-modified model.

2. A method as claimed in claim 1 comprising determining said representative line as a center line in said coronary sinus vessel tree between said opening and said implantation site.

3. A method as claimed in claim 2 comprising determining said center line as an average of a center line of said coronary sinus vessel tree during a diastolic phase of the heart and a center line of the coronary sinus vessel tree during a systolic phase of the heart.

4. A method as claimed in claim 1 comprising generating said model with a curvature and length configured for passage through said interior surface.

5. A method as claimed in claim 1 comprising selecting said deformation properties from the group consisting of curvature resistance and torsion resistance.

6. A method as claimed in claim 1 comprising generating said model as a plurality of polygons.

7. A method as claimed in claim 1 comprising, in said virtual implantation, generating a computerized representation of at least one of intensity of contact between said model and said interior wall, curvature of the model with respect to said interior wall, and torsion of the model with respect to said interior wall.

8. A method as claimed in claim 7 comprising providing feedback, selected from the group consisting of haptic feedback and tactile feedback, of said computerized representation, to an operation via an interface during said virtual implantation.

9. A method as claimed in claim 1 comprising producing said actual electrode at a production apparatus located at a common site with a location at which said virtual implantation is conducted.

10. A method as claimed in claim 1 comprising electronically transmitting electronic data representing said model to an off-site production location remote from a location at which said virtual implantation is conducted, and producing said actual electrode at said off-site location.

11. A method as claimed in claim 1 comprising implanting said actual electrode at said implantation site.

12. A method as claimed in claim 1 comprising, after implantation, monitoring a success of said implantation by obtaining an image of said actual electrode implanted at said implantation site.

13. A method as claimed in claim 12 comprising obtaining a dynamic series of images of said actual electrode at said implantation site.

14. A system for producing a patient-specific implantable pacemaker electrode, comprising:
- a computerized display;
- a computer configured to use an electronic 3D representation of the coronary sinus vessel tree of a patient in whom a pacemaker electrode is to be implanted, said 3D representation including an indication of an implantation site in the coronary sinus vessel tree for a pacemaker electrode having a mechanical structure comprising an elongate lead body terminating in an electrode tip, and segments the 3D representation of the coronary sinus vessel tree to visually indicate, at said display, the interior surface of the coronary sinus vessel tree and a representative line from an opening of the coronary sinus vessel tree to the implantation site, and generates a computerized model of only of said mechanical structure of said electrode, and including computerized deformation properties in said model that model mechanical behavior of said electrode in response to mechanical influences on said mechanical structure;
- an interface connected to said computer configured to allow an operator to conduct a computerized virtual implantation of said electrode through said 3D representation of said coronary sinus vessel tree to said implantation site using at least said model and said internal surface and said representative line, including simulating deformation of said electrode caused by a size and shape of said coronary sinus vessel tree and said deformation information, at said display to allow said operator, from said deformation in said virtual implantation, to make an implantation determination as to whether an electrode conforming to said model can be guided to and implanted at said implantation site in a medically acceptable manner;
- an electrode production apparatus that, if said implantation determination is positive, produces an actual electrode conforming to said model; and
- if said implantation determination is negative, said interface allowing iterative modification of said model and repetition of said virtual implantation until a positive implantation determination is achieved by a last-modified model, and said electrode production apparatus and then producing an actual electrode conforming to said last-modified model.

15. A system as claimed in claim 14 wherein said computer determines said representative line as a center line in said coronary sinus vessel tree between said opening and said implantation site.

16. A system as claimed in claim 15 wherein said computer determines said center line as an average of a center line of said coronary sinus vessel tree during a diastolic phase of the heart and a center line of the coronary sinus vessel tree during a systolic phase of the heart.

17. A system as claimed in claim 14 wherein said computer generates said model with a curvature and length adapted for passage through said interior surface.

18. A system as claimed in claim 14 wherein said computer selects said deformation properties from the group consisting of curvature resistance and torsion resistance.

19. A system as claimed in claim 14 wherein said computer generates said model as a plurality of polygons.

20. A system as claimed in claim 14 wherein said computer, in said virtual implantation, generates a computerized representation of at least one of intensity of contact between said model and said interior wall, curvature of the model with respect to said interior wall, and torsion of the model with respect to said interior wall.

21. A system as claimed in claim 20 wherein said interface includes a feedback unit, selected from the group consisting of haptic feedback units and tactile feedback units, that provides feedback to said operation as to said computerized representation during said virtual implantation.

22. A system as claimed in claim 14 wherein said production apparatus is located at an off-site production location remote from a location at which said virtual implantation is conducted, and comprising a data transmission arrangement that transmits data representing said model to said off-site location.

23. A system as claimed in claim 14 comprising an imaging system that, after implantation, obtains an image of said actual electrode implanted at said implantation site.

24. A system as claimed in claim 23 wherein said imaging system obtains a dynamic series of images of said actual electrode at said implantation site.

* * * * *